United States Patent [19]

Deibert

[11] 4,271,831
[45] Jun. 9, 1981

[54] KNEE BRACE

[76] Inventor: Daniel T. Deibert, 813 St. Paul St. West, Montreal, Quebec, Canada

[21] Appl. No.: 19,342

[22] Filed: Mar. 12, 1979

[51] Int. Cl.³ .............................................. A61F 5/00
[52] U.S. Cl. ...................................... 128/80 C; 2/22
[58] Field of Search ................ 128/80 C, 80 F, 80 R, 128/88, 87 R, 83; 2/22, 24, 23

[56] References Cited

U.S. PATENT DOCUMENTS

| | | | |
|---|---|---|---|
| 431,797 | 7/1890 | Blattmachr | 128/80 F |
| 559,835 | 5/1896 | Allen | 128/88 |
| 575,199 | 1/1897 | Autenrieth | 128/88 |
| 932,177 | 8/1909 | Roth | 128/80 F |
| 2,144,641 | 1/1939 | Snyder | 128/80 C |
| 2,195,024 | 3/1940 | Bullock | 128/88 |
| 2,433,570 | 12/1947 | Markkula | 128/80 F |
| 3,528,412 | 12/1970 | McDavid | 128/80 C |
| 4,136,404 | 1/1979 | Lange | 128/80 R |

FOREIGN PATENT DOCUMENTS 2724586  1/1978  Fed. Rep. of Germany ........ 128/80 C

*Primary Examiner*—Robert W. Michell
*Assistant Examiner*—Arthur S. Rose
*Attorney, Agent, or Firm*—Robert J. Schaap

[57] ABSTRACT

The present invention relates to a knee brace comprised of upper and lower sections adapted to be hinged at the knee joint of the wearer, the lower section including a rigid brace bar about the front of the tibia and a device for drawing the tibia into a desired position, with the upper section including a drift control device. The knee brace is particularly suitable for use by those with torn or otherwise injured posterior cruciates.

18 Claims, 5 Drawing Figures

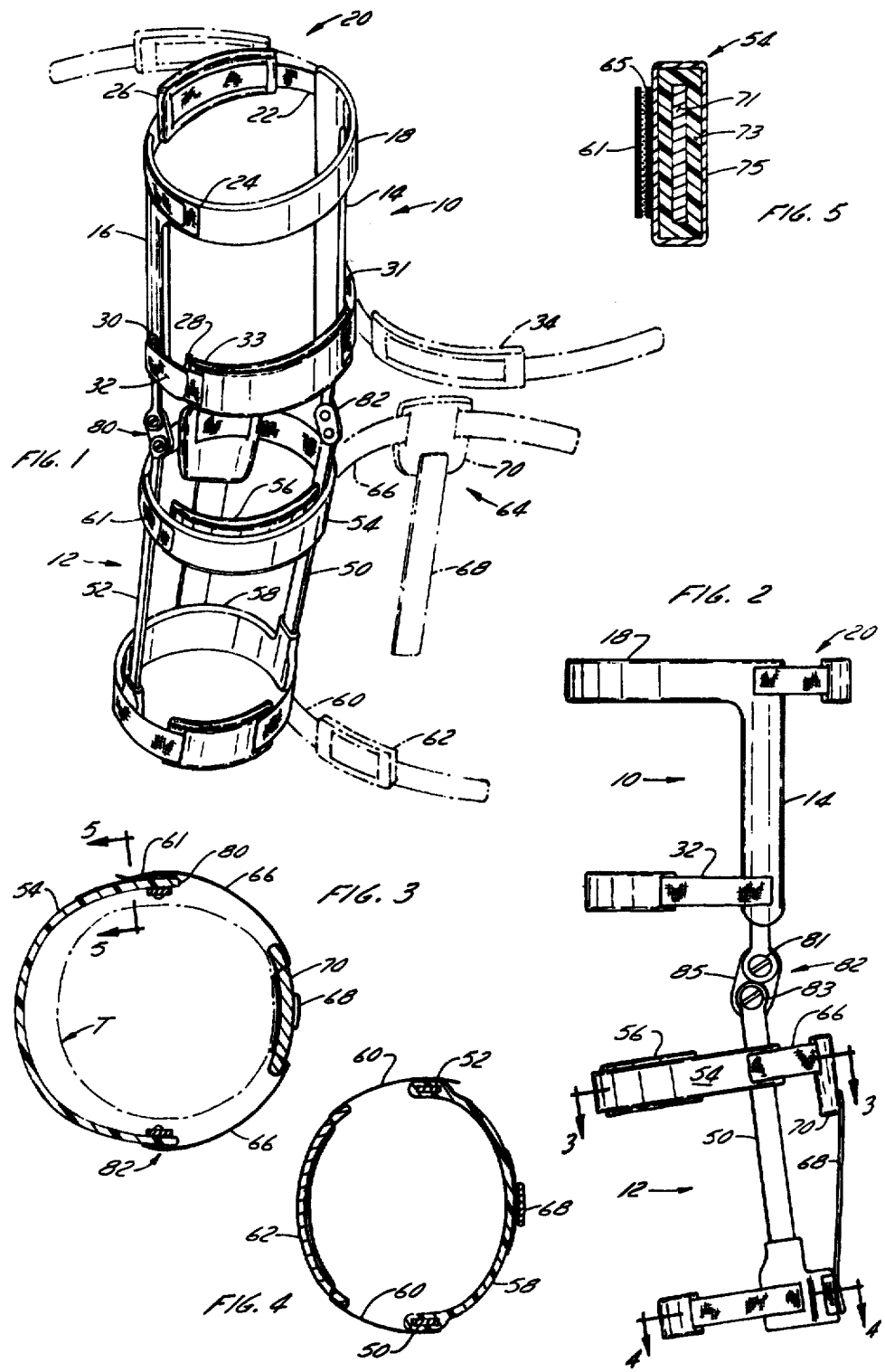

KNEE BRACE

The present invention relates to a knee brace and more particularly, relates to a hinged knee brace suitable for use in protecting torn or otherwise damaged posterior cruciates.

The use of knee braces by people suffering from torn, stretched, or otherwise damaged ligaments is well known in the art. Thus, for example, reference may be had to U.S. Pat. Nos. 618,097; 1,228,113; 2,144,641; 2,308,776; 3,528,412; 3,581,741 and 3,669,105, all of which disclose various types of knee braces for protection of the knee joint.

It is an object of the present invention to provide a knee brace suitable for use to protect those suffering from torn, stretched, or otherwise damaged posterior cruciate ligaments. It is a further object of the present invention to provide a method for the manufacture of a novel knee brace. The knee brace will permit normal use of the knee and is particularly suitable for those involved in athletics.

According to one aspect of the present invention, there is provided a knee brace having upper and lower sections which are pivotably connected together. The lower section, adapted to fit the lower or shin area of the wearer, includes a frame portion preferably comprising a pair of side frame bars. A brace bar extends anteriorly of the frame bars and is adapted to partially encircle the tibia of the wearer. Associated with the frame bar is a "hammock" device for drawing the tibia forward to the desired position. The upper section includes a "drift control means" adapted to partially encircle the lower thigh of the wearer and to control placement and movement of the knee brace. The upper section includes a frame again preferably comprising a pair of side frame bars with reinforcing means associated therewith.

In greater detail, and according to preferred embodiments of the invention, the upper and lower sections are, as previously discussed, pivotably or hingedly connected to each other to permit a normal movement at the knee joint. The pivoting or hinging may be accomplished by any suitable means—i.e. many different types of hinge assemblies are known and may be employed in the practice of the present invention.

The lower section of the knee brace includes a frame which, as previously mentioned, is preferably in the form of a pair of opposed side frame bars adapted to fit along the sides of the shin or tibia area of the wearer. A brace bar extends between the two side frame bars and is adapted to fit anteriorly of the tibia. The brace bar is a rigid member and is situated near the hinging of the two sections so as to be proximate the knee joint of the wearer. The brace bar is, when initially fitted to the wearer, spaced from the tibia by a distance of from between one and two inches. It is important that the brace bar not contact the tibia.

Associated with the brace bar is a "hammock device" which comprises means for drawing the tibia forward to the desired position and securing means to maintain it there. To this end, the hammock device preferably comprises a strap or like member which encircles the rear of the tibia and extends from one side brace bar to a further side brace bar. The member has a securing means associated therewith such that once the tibia is drawn forward to the desired position, the member can be secured in this position. Thus, an ordinary strap with suitable fastening means such as marketed under the Trade Mark "VELCRO" may be employed.

The lowermost portion of the lower section preferably includes a reinforcing bar to supply rigidity to the brace and may further include further means for securing and attaching this section of the brace to the leg. Preferably, such reinforcing means would be proximate the lowermost end of the lower section and the reinforcing means may be formed integrally with the side frame bars if so desired. The lower section preferably extends a substantial distance down the tibia to be spaced from the ankle bone.

The upper section of the brace, in a manner common to the lower section of the brace, includes frame means preferably comprising a pair of side brace bars adapted to fit along the sides of the thighs of the wearer.

The upper section includes, as aforementioned, a "drift control means" for controlling the positioning of the brace and for maintaining the same in the desired position during use. Preferably, the drift control means comprises a flexible member extending between the side frame bar about the anterior of the thigh. Means for securing the member in the desired position are provided.

The upper section of the brace also includes reinforcing means and means for securing the same to the thigh of the wearer. Accordingly, there may be provided a rigid or substantially rigid reinforcing bar adapted to partially encircle the thigh anterior. Means for securing the upper portion in the desired position may also be provided—i.e. a strap with an associated buckle or Velcro arrangement may be employed.

The rigid portions of the knee brace may be of any suitably strong yet lightweight material; such materials are well known to those skilled in this particular art. As will readily be appreciated, the device is preferably as light as possible while maintaining the necessary strength and rigidity thereby providing the maximum comfort for the user thereof. Where employed, the reinforcing means may be formed integrally with the device as a one-piece unit or in the alternative, suitable means for attaching the same to the side bars may be employed. Similarly, the flexible portions of the brace will be manufactured of suitable material known to those skilled in the art and suitable means for securing and adjusting such flexible member may be employed. Where appropriate, padding material may be used in conjunction with the structural components of the invention. Still further, it will be appreciated that in lieu of the particular frame bars disclosed, various alternatives may be employed.

Having thus generally described the invention, reference will be made to the accompanying drawings illustrating an embodiment thereof, in which:

FIG. 1 is a perspective view of the knee brace according to the present invention;

FIG. 2 is a side elevational view thereof;

FIG. 3 is a sectional view taken along the line 3—3 of FIG. 2;

FIG. 4 is a sectional view taken along the line 4—4 of FIG. 2; and

FIG. 5 is a cross-sectional view taken along the line 5—5 of FIG. 3.

Referring to the drawings in greater detail, and by reference characters thereto, there is illustrated in FIG. 1 a knee brace comprising an upper section generally designated by reference numeral 10 and a lower section generally designated by reference number 12.

Upper section 10 includes a pair of opposed side frame bars 14 and 16 adapted to fit along the sides of the thigh of the wearer. At the uppermost end of bars 14, 16 is a rigid reinforcing bar 18 which is integral with side frame bars 14 and 16 and which reinforcing bars 18 is adapted to encircle the anterior portion of the thigh. Associated with bar 18 is a retaining means 20 comprising a strap 22 having a first end secured to bar 14, the other end of strap 22 having a first mating portion of Velcro thereon adapted to be secured to a second mating Velcro portion 24. Strap 22 passes through and retains a suitable padding member 26 adapted to seat on the back of the thigh of the wearer.

At the lower portion of side frame bars 14 and 16, and extending therebetween, is a drift control means generally designated by reference numeral 28. Drift control means 28 comprises a strap having a first end secured to eyelet 30 on side frame bar 16. The free end of strap 32 is then passed through a second eyelet 31 on side frame bar 14. Strap 32 is then folded back on itself and secured by means of a Velcro attachment system. If desired, and as shown in the drawings, padding 34 and 33 may be provided on the strap 32.

Lower section 12 also includes a pair of opposed side frame bars generally designated by reference numerals 50 and 52. Side frame bars 50 and 52 are adapted to fit along the sides of the lower leg or tibia portion of the wearer. Situated proximate the upper extremity of side frame bars 50 and 52 is a rigid brace or bridge bar 54. Bridge bar 54, as may be seen from the drawings, is adapted to partially encircle the anterior portion of the tibia. Padding 56 may be provided on the interior thereof. In all cases, it is essential that bridge bar 54 be spaced from the tibia of the wearer.

Associated with bridge or brace bar 54 is a hammock device generally designated by reference numeral 64. Hammock device 64 is adapted to extend about the calf or posterior portion of the tibia of the wearer. As may be seen from FIGS. 1 and 3, hammock device 64 comprises a strap 66 having one end thereof secured to side brace bar 50. Strap 66 then extends about the posterior portion of the tibia with the opposed end adapted to partially overlap bridge or brace bar 54 and to be secured thereto by suitable attachment means such as Velcro tape 61.

Hammock device 64 also includes a pad 70 adapted to seat on the calf of the leg and a downwardly depending strap 68.

At the lower extremity of side brace bars 50 and 52, there is provided a rigid reinforcing bar 58 adapted to partially encircle the rear of the tibia proximate the ankle of the wearer. Associated with rigid reinforcing bar 58 is a securing device consisting of strap 60 with padding 62 thereon. Strap 60 is secured to bar 58 by suitable means such as a fastening tape. It will be noted that downwardly depending strap 68 of hammock device 64 is also secured to rigid reinforcing bar 58 by suitable attachment such as Velcro.

Upper section 10 and lower section 12 are joined together through the side brace bar by hinge assemblies 80 and 82. Thus, side brace bar 16 and side brace bar 52, of upper section 10 and lower section 12 respectively, are pivotably secured together by assembly 80. A similar arrangement is employed with respect to side brace bars 14 and 50. As shown in the drawings and referring to FIG. 2, a hinging member 85 may be employed with a separate pin 81 operative with brace bar 14 and a further pin 83 operative with brace bar 50. This "double" hinging action may be employed, if so desired, or the arrangement may be such that there is only a single hinging action or pivot point.

As shown in FIG. 5, bridge or brace bar 54 may comprise an inner core 71 which is rigid in nature and formed of a suitable strong yet lightweight material such as a suitable grade of steel. A padding 73 may surround the inner core 71 with an outer fabric covering 75 being provided. At one end thereof, where strap 61 is adapted to be secured, a first portion 65 of a mating Velcro-type securing system may be provided, the first portion 65 adapted to mate with a second portion on tape 61 as shown in FIG. 5.

In operation, and referring to FIG. 3, following insertion of the leg in the brace, the lower leg portion of the wearer as shown in dot-dash lines designated by reference character T in FIG. 3, is such that the front edge of the tibia is spaced a distance of from between 1½ and 2½ inches from bridge bar 54. Strap 66 of hammock device 64 is then tightened to draw the tibia forward closer to bridge bar 54, but still spaced therefrom. Following the drawing forward, strap 66 is secured to bridge bar 54. Similarly, strap 68 is secured to reinforcing bar 58. The brace is then adjusted through drift control means 28—i.e. strap 32 is drawn to the desired degree of tightness to control the movement of the brace on the knee. Straps 60 and 22 are secured in a conventional manner.

It will be understood that changes and modifications may be made to the above-described embodiment without departing from the spirit and scope of the invention. Thus, the various rigid components discussed above may be formed of any suitable material and may be formed as one-piece units or in the alternative, and in many instances it is preferable, separate components may be utilized with suitable fastening means. This is desirable for certain of the components to maintain a custom fit for the particular wearer of the brace. Furthermore, it will be understood that conventional adjustments and modifications may be made to the brace. Thus, for example, suitable padding may be provided proximate hinge assemblies 80 and 82 to maintain contact with the side of the knee joint and to provide protection therefor. Such padding may be rotatably or pivotally connected to the pivot assemblies 80 and 82.

The embodiments of the invention in which an exclusive property or privilege is claimed are defined as follows:

1. In a knee brace having an upper section adapted to seat on the thigh of a wearer and a lower section adapted to seat on the lower leg portion, with a pivot means pivotally securing the upper and lower sections together the improvement wherein said lower section includes, immediately below the point of pivoting, and immediately below the knee joint of the leg of the wearer, a rigid bridge bar means adapted to partially encircle the anterior of the lower leg, flexible drawing means associated with said rigid means and adapted to encircle the posterior of the lower leg in the same region as the rigid bridge bar means, such that the drawing means is also immediately below the knee joint of the wearer, said drawing means being adjustable and adapted to draw the tibia of the lower leg forward proximate to and spaced from said rigid means, said upper section comprising drift control means having an adjustable length with respect to said upper section and encircling the anterior of the thigh immediately above the knee joint of the wearer, said drift control means being adapted to draw the lower portion of the thigh posteriorly for controlling the drift of the brace, said drift control means cooperating with said bridge bar means to aid in protecting posterior cruciate ligaments by at least forcing the tibia into alignment with the femur, and additional means on said upper section located above said drift control means for attaching the brace to the leg of a user.

2. The improvement in the knee brace of claim 1 wherein a means is adapted to encircle the lower portion of the leg at the lower end of said lower section substantially below said bridge bar and flexible drawing means.

3. The improvement in the knee brace as defined in claim 1 wherein said upper section rigid frame and said lower section rigid frame each comprises a pair of side frame bars adapted to extend along the side of the leg of the wearer, said pivot means comprising a hinge and said upper and lower side frame bars being secured together by means of said hinge.

4. The improvement in the knee brace of claim 3 wherein said bridge bar extends between said side frame bars, and said flexible drawing means encircling posteriorly of the leg comprises a flexible strap extending from one of said side frame bars to the other of said side frame bars, said strap having a further downwardly depending strap extending therefrom.

5. A knee brace comprising an upper section and a lower section, said upper and lower sections being hingedly secured together, said upper section comprising a rigid frame, reinforcing means at the upper extremity thereof to completely encircle an upper thigh portion of a wearer, said reinforcing means having a rigid member adapted to extend anteriorly of the leg of a user and being rigidly attached to said frame and also having a member which is openable and closeable with respect to said frame and forming a continuous loop when closed, a flexible member proximate the lower portion of said upper section and immediately above the point of hinging, and the knee joint of the user, said flexible member being adapted to partially encircle the anterior of the thigh for drawing the lower portion of the thigh posteriorly and controlling drift of the brace, said flexible member being adjustable and having means for securing the same in a desired position, said lower section comprising a rigid frame, a rigid bridge bar rigidly attached to said frame and adapted to extend anteriorly of the device and of the leg of the user immediately below the point of hinging and the knee joint of the user and adapted to support the tibia of the leg and to be spaced therefrom, flexible means encircling posteriorly of the leg of the wearer associated with the bridge bar and in the same region as the bridge bar and being adapted to draw the tibia forward so that it is proximate to and also spaced from said bridge bar, means for securing the same in place so that said bridge bar and flexible means form a continuous loop when said flexible means is secured in place, and lower supporting means at the lower extremity of said lower section for securing the brace, said lower supporting means comprising a rigid member rigidly attached to said lower section and extending posteriorly of the device and of a user's leg, said lower supporting means also having a flexible member in the same region as the rigid member of the lower supporting means and being openable and closeable with respect to the lower section to thereby form a continuous loop when closed such that one must step into and through the brace in order to use the same.

6. A knee brace as defined in claim 5 wherein said upper section rigid frame and said lower section rigid frame each comprises a pair of side frame bars adapted to extend along the side of the leg of the wearer, said upper and lower side frame bars being secured together by means of a hinge.

7. The knee brace of claim 6 wherein said bridge bar extends between said side frame bars, and said means encircling posteriorly of the leg comprises a flexible strap extending from one of said side frame bars to the other of said side frame bars, said strap having a further downwardly depending strap extending therefrom.

8. The knee brace of claim 7 wherein said lower section rigid member which extends posteriorly of the leg of the wearer has said downwardly depending strap secured thereto.

9. A knee brace having an upper section adapted to seat on the thigh of a wearer and a lower section adapted to seat on the lower leg portion, a hinge mechanism pivotally securing the upper and lower sections together and which hinge mechanism is designed to be located in the region of the knee joint when the brace is worn by a user, said lower section including, immediately below the point of pivoting, and immediately below the knee joint of the leg of the wearer, a rigid bridge bar adapted to partially encircle the anterior of the lower leg and to provide support for the tibia when the brace is used, flexible drawing means associated with said rigid bridge bar and adapted to encircle and engage the posterior of the lower leg, in the same region as the bridge bar so that the drawing means is also immediately below the knee joint of the wearer, said drawing means being adjustable and adapted to draw the tibia of the lower leg forward proximate to and spaced from said rigid means, said upper section comprising a drift control strap having means to provide an adjustable length with respect to said upper section, said drift control strap encircling the anterior of the thigh immediately above the knee joint of the wearer for drawing the lower portion of the thigh posteriorly and controlling the drift of the brace, and also maintaining alignment of the hinge mechanism with the knee joint when the brace is used, said combination of the rigid bridge bar and flexible drawing means and drift control bar being adapted to maintain alignment of the tibia with the femur and thereby aid in protecting posterior crutiate ligaments by at least forcing the tibia into alignment with the femur, and additional means on said upper section located above said drift control bar for attaching the brace to the leg of a user.

10. A knee brace as defined in claim 9 wherein said upper section is comprised of a rigid frame and said lower section is comprised of a rigid frame.

11. A knee brace as defined in claim 9 wherein said upper section comprises a rigid frame, said additional means is located at the upper extremity of said upper section and adapted to encircle an upper thigh portion of a wearer.

12. A knee brace as defined in claim 11 wherein said lower section comprises a rigid frame, means at the lower extremity of said lower section for securing the brace.

13. A knee brace as defined in claim 12 wherein said upper section rigid frame and said lower section rigid frame each comprises a pair of side frame bars adapted to extend along the side of the leg of the wearer, said upper and lower side frame bars being secured together by means of a hinge.

14. A knee brace as defined in claim 13 wherein said bridge bar extends between said frame bars, and said flexible drawing means encircling posteriorly of the leg comprises a flexible strap extending from one of said side frame bars to the other of said side frame bars, said strap having a further downwardly depending strap extending therefrom.

15. A knee brace as defined in claim 14 wherein said lower section further includes a rigid reinforcing bar extending posteriorly of the leg of the wearer, said downwardly depending strap being secured thereto.

16. A knee brace having an upper section comprised of a rigid frame adapted to seat on the thigh of a wearer and a lower section comprised of a rigid frame adapted to seat on the lower leg portion, a hinge mechanism pivotally securing the upper and lower rigid frame sections and which hinge mechanism is designed to be located in the region of the knee joint when the brace is worn by a user, said upper section rigid frame including a flexible, adjustable drift control strap encircling the anterior of the thigh immediately above the hinge mechanism and the knee joint of the wearer for drawing the lower portion of the thigh posteriorly and controlling the drift of the brace and maintaining alignment of the hinge mechanism with the knee joint when the brace is used, reinforcing means at the upper extremity of said upper section rigid frame to encircle an upper thigh portion of a wearer and retain the brace on the thigh of a wearer, said reinforcing means having a rigid member adapted to extend anteriorly of the leg of a user and being rigidly attached to the rigid frame of said upper section and also having a member which is openable and closeable with respect to said upper section and forming a continuous loop of the reinforcing means when closed, said upper section rigid frame having a pair of upper side frame bars adapted to extend along the side of the leg of the wearer, said lower section rigid frame comprising immediately below the point of pivoting and the knee joint of the user, a rigid bridge bar rigidly attached to the rigid frame of said lower section and adapted to partially encircle the anterior of the lower leg and provide support for the tibia when the brace is used, flexible drawing means associated with said rigid bridge bar and adapted to encircle the posterior of the lower leg, said drawing means being adjustable and adapted to draw the tibia of the lower leg forward proximate to and spaced from said rigid bridge bar, said drawing means also being located immediately below the point of pivoting and in the same region as the bridge bar so that the bridge bar and drawing means form a continuous loop when closed, said lower section rigid frame having a pair of lower side frame bars adapted to extend along the side of the leg of the wearer, and lower supporting means at the lower extremity of said lower section rigid frame for securing the brace, said lower supporting means comprising a rigid member rigidly attached to the lower section rigid frame and extending posteriorly of the device and of a user's leg, said lower supporting means also having a flexible member in the same region as the rigid member of the lower supporting means and being openable and closeable with respect to the lower section to thereby form a continuous loop when closed such that one must step into and through the brace in order to use the same.

17. A knee brace comprising an upper section and a lower section, a hinge operatively connected to said upper and lower sections for hingedly securing said upper and lower sections together, said upper section comprising a rigid frame, a pair of side frame bars on said upper section adapted to extend along the sides of the leg of the wearer, means at the upper extremity of said upper section to encircle an upper thigh portion of a wearer, a flexible member proximate the lower portion of said upper section and proximate the point of hinging, said flexible member being adapted to partially encircle the anterior of the thigh, said flexible member being adjustable and having means for securing the same in a desired position, said lower section comprising a rigid frame, a pair of side frame bars on said lower section also adapted to extend along the sides of the leg of the wearer, said upper and lower side frame bars being secured together by said hinge, a rigid brige bar extending anteriorly of the device proximate the point of hinging and adapted to support the tibia of the leg and to be spaced therefrom, said bridge bar extending from one of the side frame bars on said lower section to the other of the side frame bars on the lower section, a flexible strap encircling posteriorly of the leg of the wearer associated with the bridge bar and being adapted to draw the tibia forward, said flexible strap extending between one of the side frame bars on said lower section to the other of the side frame bars on the lower section, means for securing the flexible strap in place, a rigid reinforcing bar at the lower extremity of said lower section for securing the brace such that one must step into and through the brace in order to use the same, said rigid reinforcing bar on said lower section extending posteriorly of the leg of the wearer, and a downwardly depending strap secured to said rigid reinforcing bar and extending downwardly from said flexible strap.

18. A knee brace having an upper section comprised of a rigid frame adapted to seat on the thigh of a wearer and a lower section comprised of a rigid frame adapted to seat on the lower leg portion, a hinge mechanism pivotally securing the upper and lower rigid frame sections and which hinge mechanism is designed to be located in the region of the knee joint when the brace is worn by a user, said upper section rigid frame including a flexible drift control strap encircling the anterior of the thigh proximate the knee joint of the wearer to draw the femur posteriorly and maintain alignment of the hinge mechanism with the knee joint when the brace is used, said flexible strap being adjustable and having means for securing the same in a desired position, means at the upper extremity of said upper section rigid frame to encircle an upper thigh portion of a wearer and retain the brace on the thigh of a wearer, said upper section rigid frame having a pair of upper side frame bars adapted to extend along the side of the leg of the wearer, said lower section rigid frame comprising proximate to the point of pivoting a rigid bridge bar extending anteriorly of the knee brace and adapted to partially encircle the anterior of the lower leg and provide support for the tibia when the brace is used, flexible drawing means associated with said rigid bridge bar and adapted to encircle the posterior of the lower leg, said drawing means being adjustable and adapted to draw the tibia of the lower leg forward proximate to and spaced from said rigid means, said lower section rigid frame having a pair of lower side frame bars adapted to extend along the side of the leg of the wearer, said bridge bar extending from one of said side frame bars to the other of the side frame bars on said lower section, said flexible drawing means extending between one of the side frame bars on said lower section to the other of the side frame bars on the lower section, means for securing the flexible strap in place, and a rigid reinforcing bar at the lower extremity of said lower section rigid frame for securing the brace, such that one must step into and through the brace in order to use the same, said rigid reinforcing bar on said lower section extending posteriorly of the leg of the wearer, and a downwardly depending strap secured to said rigid reinforcing bar and extending downwardly from said flexible strap.

* * * * *